US00PP10728P

United States Patent [19]

Olesen et al.

[11] Patent Number: Plant 10,728

[45] Date of Patent: Dec. 22, 1998

[54] MINIATURE ROSE PLANT NAMED 'POULOBE'

[75] Inventors: L. Pernille Olesen; Mogens N. Olesen, both of Fredensborg, Denmark

[73] Assignee: Poulsen Roser Aps, Fredensborg, Denmark

[21] Appl. No.: 843,475

[22] Filed: Apr. 8, 1997

[51] Int. Cl.[6] ..... A01H 5/00

[52] U.S. Cl. ..... Plt./10

[58] Field of Search ..... Plt./10, 7.1

[56] References Cited

U.S. PATENT DOCUMENTS

P.P. 5,692 3/1986 Saville ..... Plt./10
P.P. 6,244 8/1988 de Ruiter ..... Plt./10
P.P. 9,483 3/1996 Olesen et al. ..... Plt./10
P.P. 9,634 8/1996 Pouw ..... Plt./10

OTHER PUBLICATIONS

UPOV–ROM, 1997/04, Plant Variety Database, GTI Jouve Retrieval Software, citation for 'Poulobe'.

*Primary Examiner*—Howard J. Locker
*Attorney, Agent, or Firm*—Foley & Lardner

[57] ABSTRACT

A new and distinct cultivar of miniature rose plant named 'POULobe', characterized by its vigorous and upright growth habit which is suitable for forcing in 12.5 cm to 15 cm pots; high bud and flower count with excellent flower durability; stable red petal color which fades only slightly as flowers age; good disease resistance; and attractive dark-green foliage with a semi-glossy finish.

2 Drawing Sheets

The present invention comprises a new and distinct cultivar of rose plant of the miniature class, hereinafter referred to by the cultivar name 'POULobe'.

BACKGROUND OF THE INVENTION

The rose plant of the present invention has a unique combination of characteristics which are outstanding in the new variety and which distinguish it from the rose variation from which it was derived, 'POULnola', as well as all other varieties of which we are aware. Particularly distinctive characteristics of the new variety include:

1. Abundant dark-red flowers with excellent vase life;
2. Attractive long-lasting foliage and compact growth;
3. Year-round flowering under glasshouse conditions;
4. Suitability for production as a flowering pot rose from softwood cuttings in 12.5 cm to 15 cm pots;
5. Durable flowers and foliage which make the variety suitable for distribution in the floral industry.

This combination of traits was not previously present in commercial cultivars of this type. 'POULobe' was discovered by L. Pernille and Mogens N. Olesen in a controlled greenhouse environment in Fredensborg, Denmark in the Spring of 1994. 'POULobe' originated as a naturally occurring, whole-branch mutation of the Poulsen proprietary variety 'POULnola'.

Asexual reproduction of the new cultivar 'POULobe' by budding and by cutting, as performed initially by L. Pernille and Mogens N. Olesen in August of 1994 at Fredensborg, Denmark has demonstrated that the combination of characteristics as herein disclosed for 'POULobe' are firmly fixed through successive generations of asexual reproduction.

'POULobe', has not been observed under all possible environmental conditions. The phenotype may vary significantly with variations in environment such as temperature, light intensity and day length, without a change in genotype of the variety. The following observations, measurements and comparisons describe the plants grown in Fredensborg, Denmark and Half Moon Bay, Calif. under greenhouse conditions which approximate those generally used in commercial practice. Descriptions were made from plants treated with growth regulator Paclobutrazol, which was applied at 30 ppm weekly for three weeks beginning at a plant age of 8 weeks.

BRIEF SUMMARY OF THE INVENTION

The following traits have been repeatedly observed and are determined to be basic characteristics of 'POULobe'. which in combination distinguish this rose as a new and distinct cultivar:

1. Vigorous, upright pot rose variety suitable for forcing in 12.5 cm to 15 cm pots.
2. The buds and flowers are abundant and the flowers are durable.
3. Stable red petal color fades only slightly as flowers age.
4. Good disease resistance.
5. Attractive dark green foliage with semi- glossy finish.

Of the many commercial cultivars known to the present inventors, the most similar in comparison to 'POULobe' is 'POULnola'.

Comparison Chart:

| Characteristic | 'POULobe' | 'POULnola' |
|---|---|---|
| Blooms per plant | Abundant | Limited |
| Color, upperside of petal | RHS 44A | RHS 50A |
| Color, underside of petal | RHS 53C | RHS 51A |

The comparison chart compares certain characteristics of 'POULobe', to those same characteristics of 'POULnola'. In general, 'POULobe' has more flowers and darker red flowers than 'POULnola'.

BRIEF DESCRIPTION OF THE DRAWINGS

The accompanying photographic drawings show typical inflorescence and foliage characteristics of 'POULobe', with the colors being as nearly true as possible with illustrations of this type.

Sheet 1 shows a side view of a potted plant.

Sheet 2 shows (1) a side view of the plant with flowers, (2) a side view of a flower, (3) petals, (4) flower parts, (5) stem with leaves and (6) leaves from 'POULobe'.

DETAILED BOTANICAL DESCRIPTION

In the following description, color references are made to The Royal Horticultural Society Color ("R.H.S.") Chart. The color values were determined in Fredensborg, Denmark.

Classification: *Botanical*: Rosa L. *Commercial*: 'POULobe'.
Parentage: A mutation of the variety 'POULnola'.
Plant:

*General Appearance.*—Habit: Compact, bushy. Growth: Dwarf, upright. Size: When grown in a greenhouse as a 15 cm pot plant, the average height of the plant itself is 24 to 26 cm and the average width is 17 to 22 cm. When grown as a nursery plant on its own roots, the average plant height is 30 to 40 cm and the average width is 25 to 35 cm. Rachis: Color is R.H.S. 147 C. Canes: Green, straight, or nearly so. Main Stems: Strong, upright, with limited vegetative side shoots. Straight, or nearly so. Smooth. Color is R.H.S. 138 A. Thorns: Present on stem, to 4 mm in length, slightly concave to needle shaped, thorns on upper portion of the stem are R.H.S. 49D and thorns on the lower portion of the stem are 49B. Branches: Ordinary.

*Foliage.*—Leaves: Number: Mostly 5 leaflets. Average abundance of foliage. Shape: Leaflets are ovate. Appearance: Semi-glossy to glossy, margins serrated, leaflets generally flat. Color (topside): Medium dark green, R.H.S. 147A, of the Green-Yellow Group. Juvenile foliage is 146 A.

Color (bottom side): Medium green, R.H.S. 148B, of the Green-Yellow Group. Bottom side of upper-leaves that are expanding as plants come into bloom can have reddish pigment. Juvenile foliage is R.H.S. 147C and the reddish coloration on the underside of the juvenile foliage is 42B. Stipules: Present, well formed, to 10 mm from base to tip. With stiff hairs on margin. Color is R.H.S. 147 A. Other foliage characteristics: Mean petiole length is 15 mm. Mean entire leaf length is 70 mm. Mean width of entire leaf is 48 mm.

Flowers:

*Borne.*—Generally as a simple monochasium or dichasium inflorescence.

*Type of stems.*—Upright pedicels.

*Number of flowers (per stem).*—Generally with multiple buds, from 2 to 4 per flowering stem.

*Ouantity of blooms.*—In pots with four plants, generally up to 5 to 7 blooms per plant.

*Buds.*—Pointed. Pedicel length: 40 to 45 mm Pedicel surface: With stiff hairs and small prickles. Pedicel strength: Good. Bud shape: Pointed until the petals begin to unfurl, then becomes globular. Bud color: R.H.S. 53C of the Red Group, when bud is ¼ open. Receptacle color: R.H.S. 137D of the Green Group. Lighter in color than sepals. Receptacle shape: Urn shaped. Small in size. Receptacle surface: Smooth, glabrous. Sepals color: Green. R.H.S. 137B of the Green Group. Sepals surface texture: Covered in fine hairs. Three of the five sepals have moderately developed foliaceous appendages. Margins have small stiff hairs.

*Blooms.*—Numerous, small red flowers with slightly reflexed petals. Size: Open flowers are 35 mm to 40 mm in diameter. Petalage: Double to very double. Approximately 35 to 40 petals per flower. Length: Length is 14 mm to 16 mm from base of sepal attachment to end of flower bud. Length of the individual petal is 15–20 mm. bud. Texture: Petal is smooth, with weak undulation at the edge. Petal has a firm substance. Shape: Open flower form is a flattened convex, when viewed from the side. When viewed from the top, open flowers are round. Color: Upperside: R.H.S. 44A of the Red Group upon opening. Color fades slightly to R.H.S. 44B of the Red Group after flower has been open over a week. A small base petal spot exists, R.H.S. 4D of the Yellow Group. Underside: R.H.S. 53C of the Red Group. Fades slightly to R.H.S. 53D of the Red Group after flower is open a number of days. The lighter midrib on the bloom undersurface is R.H.S. 55D.

*Keeping quality.*—Blooms last 15 days on plant and 12 days as a cut flower.

*Fragrance.*—Absent or very limited.

*Reproductive organs.*—Stamens: Present, attached uniformly around flower. Filaments: R.H.S. 5B, pale green to white in color, upright, somewhat irregular in length. Anthers: R.H.S. 181A in color. Anthers are inferior in position to stigmas. Pistils: Present, moderately abundant. Pale green to white in color. Stigmas: Superior in position in relationship to stamens. Color is R.H.S. 157A with intonations of R.H.S. 37D. Styles: Upper portion may have light pink-red coloration, is R.H.S.157A. Style lightly pubescent. Ovaries: Inferior.

Disease resistance: The variety has demonstrated good resistance to Mildew, Blackspot and rust.

What is claimed is:

1. A new and distinct cultivar of rose plant named 'POULobe', as illustrated and described.

* * * * *

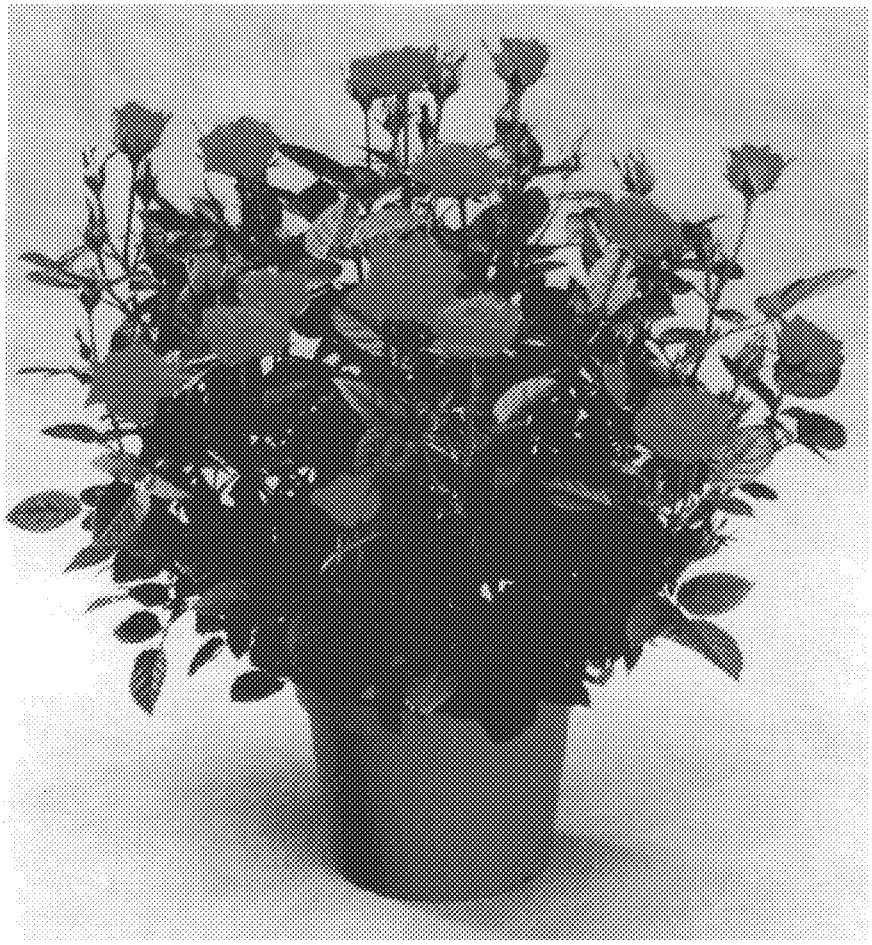

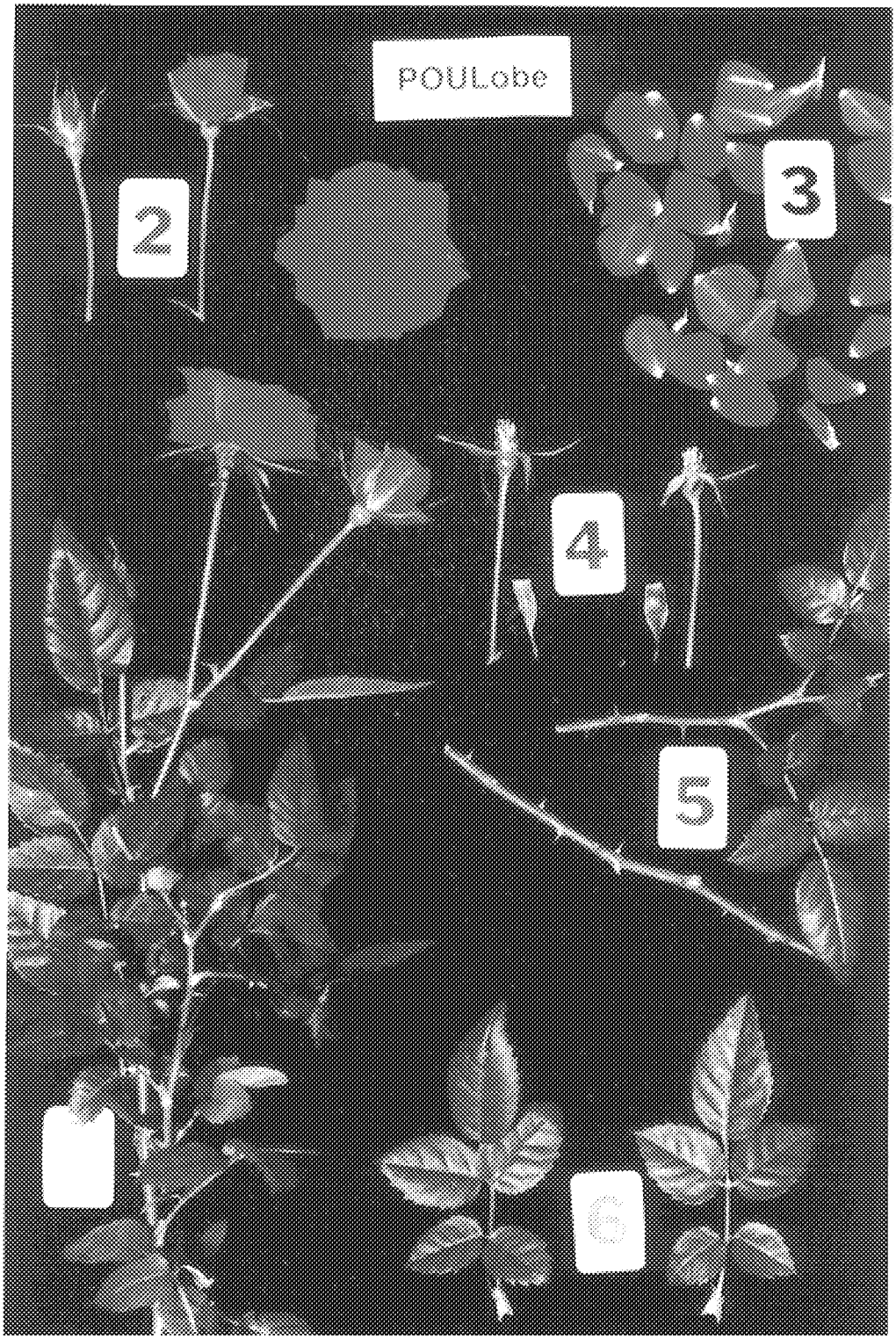
POULobe
2
3
4
5
6